(12) United States Patent
Birchler et al.

(10) Patent No.: US 11,540,898 B2
(45) Date of Patent: Jan. 3, 2023

(54) BONE SCREW WITH FRANGIBLE TRACKING TAG

(71) Applicant: Nexxt Spine, LLC, Noblesville, IN (US)

(72) Inventors: Chad Birchler, Kokomo, IN (US); Austin Clemens, Indianapolis, IN (US); Alaedeen Abu-Mulaweh, Noblesville, IN (US); Andrew Elsbury, McCordsville, IN (US)

(73) Assignee: Nexxt Spine, LLC, Noblesville, IN (US)

( * ) Notice: Subject to any disclaimer, the term of this patent is extended or adjusted under 35 U.S.C. 154(b) by 586 days.

(21) Appl. No.: 16/571,254

(22) Filed: Sep. 16, 2019

(65) Prior Publication Data

US 2020/0093565 A1 Mar. 26, 2020

Related U.S. Application Data (60) Provisional application No. 62/734,680, filed on Sep. 21, 2018.

(51) Int. Cl.
| | |
|---|---|
| *A61B 90/90* | (2016.01) |
| *A61B 17/86* | (2006.01) |
| *A61B 90/00* | (2016.01) |
| *A61B 17/80* | (2006.01) |

(52) U.S. Cl.
CPC .......... *A61B 90/90* (2016.02); *A61B 17/8635* (2013.01); *A61B 17/8085* (2013.01); *A61B 2090/037* (2016.02)

(58) Field of Classification Search
CPC .................................................. F16B 1/0071
See application file for complete search history.

(56) References Cited

U.S. PATENT DOCUMENTS

| | | | | |
|---|---|---|---|---|
| 4,923,471 | A * | 5/1990 | Morgan | A61B 17/8085 606/907 |
| 8,221,478 | B2 | 7/2012 | Patterson et al. | |
| 9,498,294 | B2 * | 11/2016 | Rigsby | A61B 90/40 |
| 9,911,019 | B2 * | 3/2018 | Schoutens | A61B 90/98 |
| 2008/0230423 | A1 * | 9/2008 | Loeffler | A61B 50/22 606/300 |
| 2014/0046380 | A1 * | 2/2014 | Asfora | A61B 17/1637 606/97 |
| 2014/0214097 | A1 * | 7/2014 | Jackson | A61B 17/7032 606/305 |
| 2016/0249995 | A1 * | 9/2016 | Ritchey | A61B 50/33 53/425 |

* cited by examiner

*Primary Examiner* — Tessa M Matthews
(74) *Attorney, Agent, or Firm* — Maginot, Moore & Beck, LLP (57) ABSTRACT

An implant in the form of a bone screw that meets device tracking requirements set for the in the FDA regulations is provided. The bone screw includes a screw body and a tag body formed as an integral extension of the screw body and is connected to the screw body via a frangible interface bone screw. The screw body has a head portion and a threaded shaft portion that extends along a longitudinal axis from the head portion to a screw tip of the screw body. The tag body defines at least one surface configured to display traceability information for the bone screw. The frangible interface is disposed between the tag body and the screw tip of the screw body. The frangible interface is configured to fracture upon application of a predefined mechanical force so that the tag body is removable from the bone screw.

15 Claims, 7 Drawing Sheets

BONE SCREW WITH FRANGIBLE TRACKING TAG

This application claims the benefit of U.S. Provisional Application 62/734,680, filed Sep. 21, 2018, the disclosure of which is incorporated herein by reference in its entirety.

FIELD

The present disclosure relates to tracking of medical devices and, more particularly, to frangible identification tags for bone screws.

BACKGROUND

Pursuant to Food and Drug Administration (FDA) regulations, manufacturers are required to track certain devices from their manufacture through the distribution chain. The purpose of device tracking is to ensure the ability to promptly locate devices in commercial distribution. Tracking information may be used to facilitate notifications and recalls ordered by FDA in the case of risks to health presented by the devices. In particular 21 C.F.R. Part 821 provides that manufacturers must adopt a method of tracking devices whose failure would be reasonably likely to have serious, adverse health consequences; or which is intended to be implanted in the human body for more than one year; or are life-sustaining or life-supporting devices used outside of a device user facility.

The FDA regulation identifies the information that must be provided and maintained after distribution to or implantation in a patient. This information includes: (i) The unique device identifier (UDI), lot number, batch number, model number, or serial number of the device or other identifier necessary to provide for effective tracking of the devices; (ii) The date the device was shipped by the manufacturer; (iii) The name, address, telephone number, and social security number (if available) of the patient receiving the device, unless not released by the patient; (iv) The date the device was provided to the patient; (v) The name, mailing address, and telephone number of the prescribing physician; (vi) The name, mailing address, and telephone number of the physician regularly following the patient if different than the prescribing physician; and (vii) If applicable, the date the device was explanted and the name, mailing address, and telephone number of the explanting physician; the date of the patient's death; or the date the device was returned to the manufacturer, permanently retired from use, or otherwise permanently disposed of.

In the device manufacture, the key requirement is the "identifier necessary to provide for effective tracking of the devices," which is hereinafter referred to as "traceability information." In most cases, manufacturers opt to use a unique device identifier (UDI) code to satisfy this requirement. For large implants, such as bone plates and large bone screws, the traceability information required by the FDA can be etched or laser-marked onto the implant. However, smaller implants, such as small bone screws, are not large enough or do not have enough available surface area to accept a readable UDI code.

For such smaller implants, some manufacturers attach removable tags or labels to the implants to provide additional space for the UDI code. These attached tags are usually formed from material that is different than the material of the implant, for example, plastic material, and are fixed to the implants after the implants have been manufactured. While these separately attachable tags are adequate to meet the FDA's identification requirements, the tags often add costs to the implant manufacturing process. For instance, in the case of separately attachable tags formed from plastic material, the tags will typically require dedicated forming tools, such as molding tools for the injection molding of the plastic tags. The implant manufacturing process will also include additional assembly steps to securely attach a tag to each implant.

To account for some of the issues in using separately attachable tags, some smaller implants include a removable tag that is formed integrally with the implant. U.S. Pat. No. 4,923,471 (the '471 patent) discloses a bone fracture reduction device for the internal fixation and immobilization of bone fragments. The reduction device includes a bone affixation plate that defines at least two spaced openings for receiving bone screws. The reduction device also includes a bone plate identification tag formed integrally with a peripheral portion the device. The identification tag is severable from the reduction device without effecting the attachment or function of the device due to the location of the tag on a non-functional, peripheral surface of the reduction device. More specifically, the surface from which the identification tag integrally extends from the reduction device in the '471 patent does not interact with the bone(s) of the patient, the bone screws that are inserted into the device, or the driving tool(s) that are used to attach the bone screws to the device.

The use of an integrally-formed, removable tag or label on a bone screw poses unique challenges as compared to the use of these tags on other small, implantable devices. These challenges arise because essentially every surface of a bone screw performs important functions and, thus, these functional surfaces are subject to stringent dimensional controls. For instance, the head of the bone screw typically defines a driving feature used to cooperate with a driving tool to rotatably drive the bone screw into the bone of a patient. Depending on the specific function of the bone screw, the head can also include external threads and/or smooth contact surfaces that are configured to cooperate with one or more other medical devices. Similarly, the shaft of the bone screw typically includes one or more external threads that directly interface with the bone to secure the bone screw. The tip of the bone screw can have a variety of geometries to provide the bone screw with specific functionalities, such a self-drilling.

Consequently, it would be advantageous to provide a feature that permits marking a small implant, such as a bone screw, with the information required by the FDA. It would be further advantageous to safely incorporate aspects of the provided marking feature into the functionality of the small implant.

SUMMARY

A bone screw in one embodiment includes a screw body that has a head portion and a threaded shaft portion that extends along a longitudinal axis from the head portion to a screw tip of the screw body. The bone screw also includes a tag body that defines at least one surface configured to display traceability information for the bone screw. The tag body is formed as an integral extension of the screw body and is connected to the screw body via a frangible interface disposed between the tag body and the screw tip. The frangible interface is configured to fracture upon application of a predefined mechanical force such that the tag body is removable from the bone screw.

A bone screw in another embodiment includes a screw body that has a screw head and a screw shaft that extends along a longitudinal axis from the screw head. The screw shaft defines at least one thread that helically encircles the longitudinal axis along a length of the screw shaft and terminates at a screw tip. The screw shaft is fluted such that a leading portion of the at least one thread has a cutting edge configured for self-tapping. The screw head defines a driving feature configured to cooperate with a driving tool to rotate the screw body and an outer surface configured as one of a smooth arcuate surface or a threaded surface. The bone screw further includes a tag body that has a rectangular shape and defines at least two opposed surfaces configured to display traceability information for the bone screw. The tag body is formed as an integral extension of the screw body and is connected to the screw body via a frangible interface disposed between the tag body and the screw tip. The frangible interface defines a region of reduced thickness between the screw tip and the tag body and is configured to fracture upon application of a predefined mechanical force such that the tag body is removable from the bone screw.

A method of implanting a bone screw in a bone includes providing a bone screw with a screw portion and a tag portion formed as an integral extension of the screw portion. The screw portion has a screw head and a threaded screw shaft that extends from the screw head. The tag portion defines at least one surface configured to display traceability information for the bone screw. The method further includes fracturing a frangible interface disposed between the tag portion and a tip of the screw portion. The frangible interface is fractured by applying a mechanical force to the tag portion. The method further includes removing the tag portion from the screw portion after the frangible interface is fractured and rotatably driving the screw portion into the bone such that the tip of the screw portion and frangible remains of the fractured frangible interface are positioned within the bone.

DETAILED DESCRIPTION

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains FIGS. 1-8 depict an implant that meets the device tracking requirements set for the in the FDA regulations. The implant is depicted in a first embodiment as a bone screw 10. The bone screw 10 includes a screw body 14 configured to be at least partially implanted in a bone (not shown) of a patient and a tag body 18 configured to display traceability information 20a, 20b, 20c for the bone screw 10. As explained later, the tag body 18 is connected to the screw body 14 via a frangible interface 22 such that the tag body 18 can be removed from the bone screw 10 before the screw body 14 is implanted in the bone.

Figure 7:
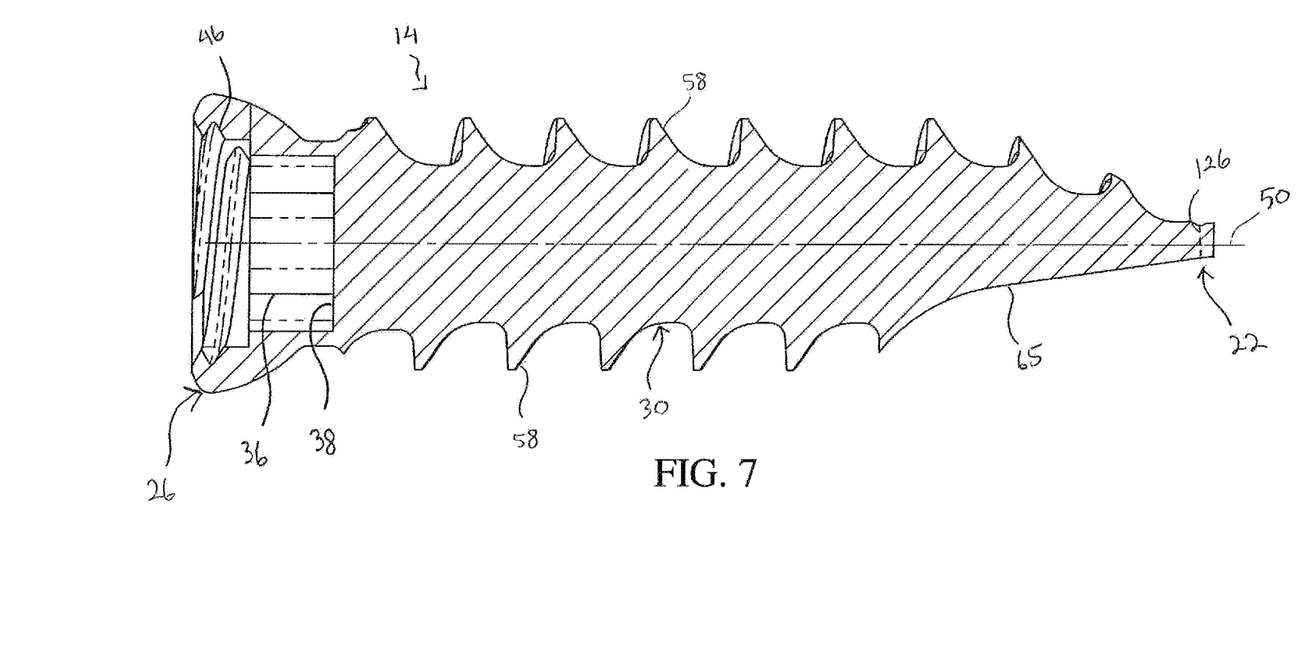
FIG. 7 is a longitudinal section view of the bone screw taken along line A-A in FIG. 6 showing yet another view of the flute extending into the tip of the bone screw and into the frangible interface.
Figure 8:
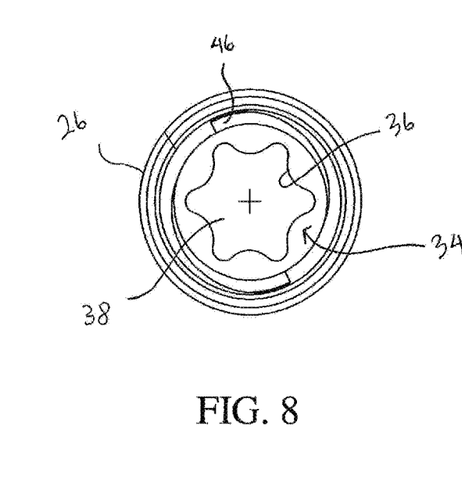
FIG. 8 is an auxiliary view of a head portion of the bone screw showing a hexalobe interface formed in the head portion.

The screw body 14 includes a head portion 26 and a threaded shaft portion 30 that extends from the head portion 26. The head portion 26 defines a driving feature 34 at a first end of the screw body 14. The driving feature 34 is configured to cooperate with a driving tool (not shown) that is used to rotate the screw body 14 into the bone. As shown in FIGS. 7 and 8, the driving feature 34 in one embodiment is a hexalobe interface disposed in a recess 38 that opens outwardly from the head portion 26 in a direction facing away from the shaft portion 30. The driving feature 34 in other embodiments can have different configurations that cooperate with the driving tool. The head portion 26 further defines an outer surface 42 that faces generally away from the first end. In the embodiment shown, the outer surface 42 is smooth and has an arcuate shape configured to cooperate with a corresponding surface in another medical device (not shown) used in connection with the bone screw 10, such as a bone plate. The head portion 26 in one embodiment also defines an internal thread 46 disposed in the recess 38 at a position longitudinally outward from the driving feature 34, as shown in FIGS. 7 and 8.

The shaft portion 30 extends from the head portion 26 along a longitudinal axis 50 of the bone screw 10 and defines a screw tip 54 at a second end of the screw body 14 spaced from the first end. The screw tip 54 generally defines a longitudinal-most extent of the shaft portion 30 along the longitudinal axis 50. The shaft portion 30 includes at least one external thread 58 that helically encircles the longitudinal axis 50 and extends between the head portion 26 and the screw tip 54. The external thread 58 in the embodiment shown extends from the screw tip 54 for the entire length of the shaft portion 30. In other embodiments, the external thread 58 extends from the screw tip 54 for less than the entire length of the shaft portion 30. The external thread 58 has a thread profile, a thread lead, and a thread pitch that enables the screw body 14 to form its own thread and advance into the bone when rotated by the driving tool (i.e., a self-tapping thread). The shaft portion 30 in some embodiments has a plurality of external threads providing the shaft portion with multiple thread starts.

Figure 1:
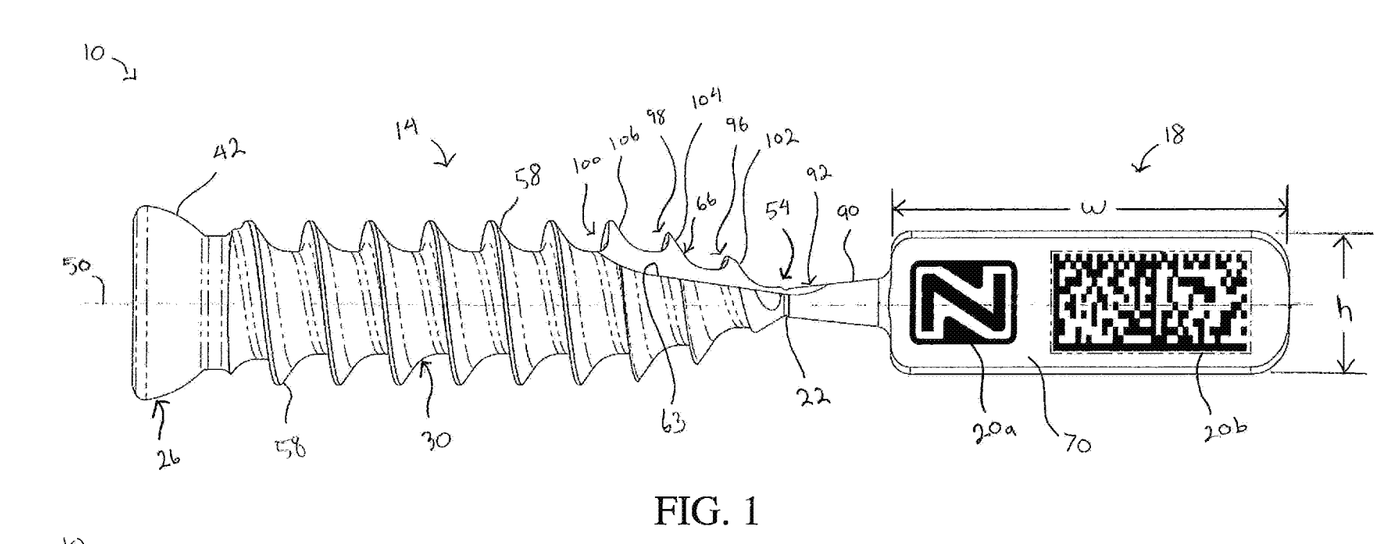
FIG. 1 is a side view of a sharp-tip bone screw incorporating the frangible tag of the present disclosure showing one side of the frangible tag.
Figure 2:
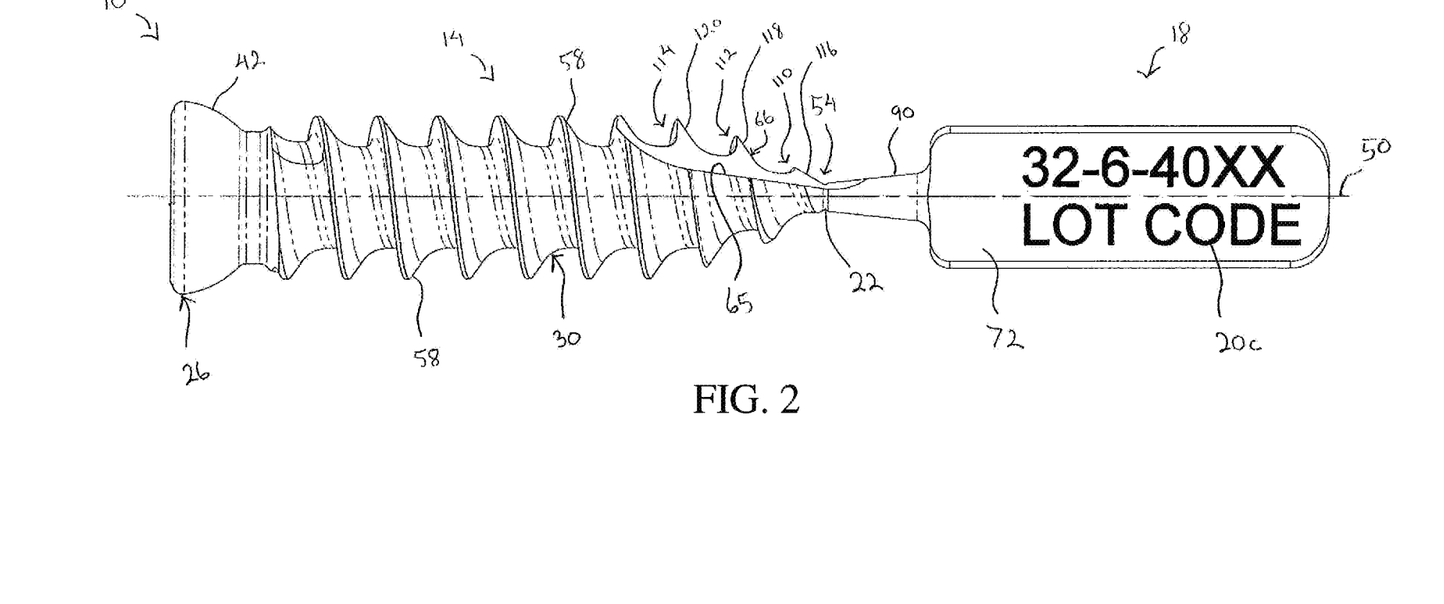
FIG. 2 is a side view of the bone screw depicted in FIG. 1 showing the opposite side of the frangible tag.

The screw body 14 has at least one flute 63, 65 that extends from the screw tip 54 into a portion of the shaft portion 30. The flute 63, 65 in the embodiment shown extends longitudinally and forms multiple gaps in the external thread 58. More specifically, the flute 63, 65 forms a single gap in the external thread 58 for each rotation of the external thread 58 about the longitudinal axis 50. As shown, the flute 63, 65 forms at least three gaps in the external thread 58 as the flute extends longitudinally along a portion of the length of the shaft portion 30. The gaps formed by the flute 63, 65 expose cutting edges 66 on leading portions of the external thread 58. The cutting edges 66 enable the external thread 58 to remove bone material from the bone when the screw body 14 is rotatably advanced into the bone (i.e., a self-cutting thread). The flute 63, 65 can have any geometry that exposes the cutting edges 66 along the shaft portion 30. As best illustrated in FIGS. 1 and 2, the screw body 14 of the exemplary embodiment has two flutes, which include a first flute 63 (FIG. 1) and a second flute 65 (FIGS. 2 and 3) arranged approximately 180° apart from the first flute 63 about the longitudinal axis 50. The first flute 63 and the second flute 65 form two gaps in the external thread 58 for each rotation of the external thread 58 about the longitudinal axis 50.

The tag body 18 is formed as an integral extension of the screw body 14 and is connected to the screw body 14 via the frangible interface 22. As used herein, the phrase "integral extension" means that the screw body 14, the tag body 18, and the frangible interface 22 are formed from the same material and that such material is seamlessly interconnected among the screw body 14, the tag body 18, and the frangible interface 22 to form a single, cohesive unit. As a first non-limiting example of bodies formed as an integral extension, the screw body 14, the tag body 18, and the frangible interface 22 can be initially formed from a single "blank" of one type of material, which is subsequently processed via one or more machining techniques. As a second non-limiting example of bodies formed as an integral extension, the bone screw 10 is formed in part by metal injection molding (MIM) such that the screw body 14, the tag body 18, and the frangible interface 22 are defined nearly simultaneously in a molding step using one type of material. As used herein, the term "frangible" means any mechanism by which the tag body 18 that is integrally formed with the screw body 14 can be removed from the screw body 14 by application of mechanical force.

Figure 3:
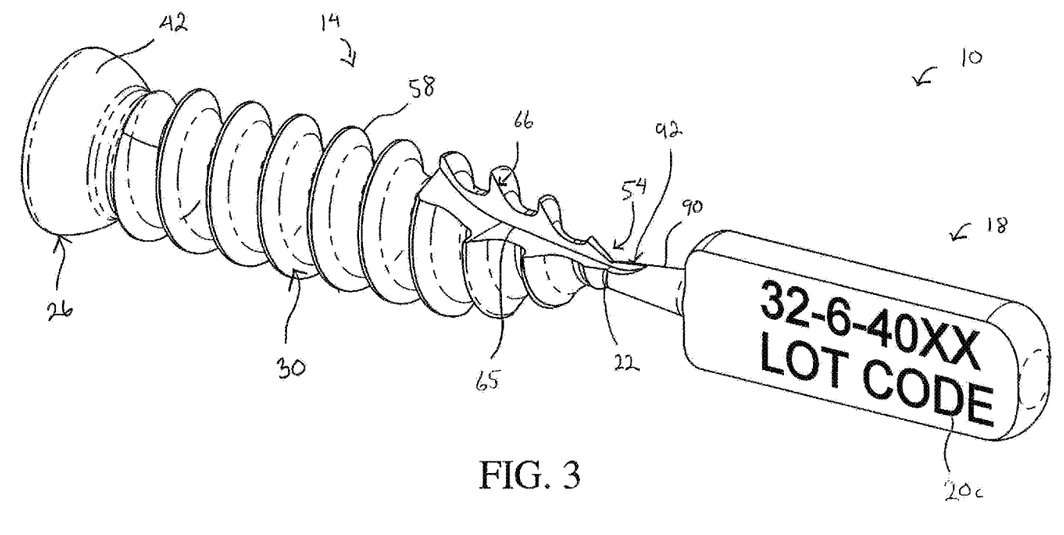
FIG. 3 is a perspective view of the bone screw depicted in FIG. 2 showing a flute extending into a tip of the bone screw and into a portion of the frangible interface.

With reference to FIGS. 1-3, the tag body 18 defines a first surface 70 configured to display the traceability information 20a, 20b, 20c for the bone screw 10. As shown in FIG. 1, the first surface 70 can include a manufacturer identifier, such as logo 20a, and a scannable code, such as a bar code or the QR code 20b. The scannable code corresponds to the unique device identifier (UDI) code for the bone screw 10 and provides access to additional information as desired. The tag body 18 in the embodiment shown is configured as a generally rectangular plate. The tag body 18 in this embodiment defines a second surface 72 that faces opposite the first surface 70 so that additional information can be provided on the second surface 72, as shown in FIG. 2. This additional information can be the batch number and lot code 20c, as illustrated. The traceability information 20a, 20b, 20c on the tag body 18 can be etched or laser marked, and/or can be printed in a manner that is suitably permanent.

Figure 6:
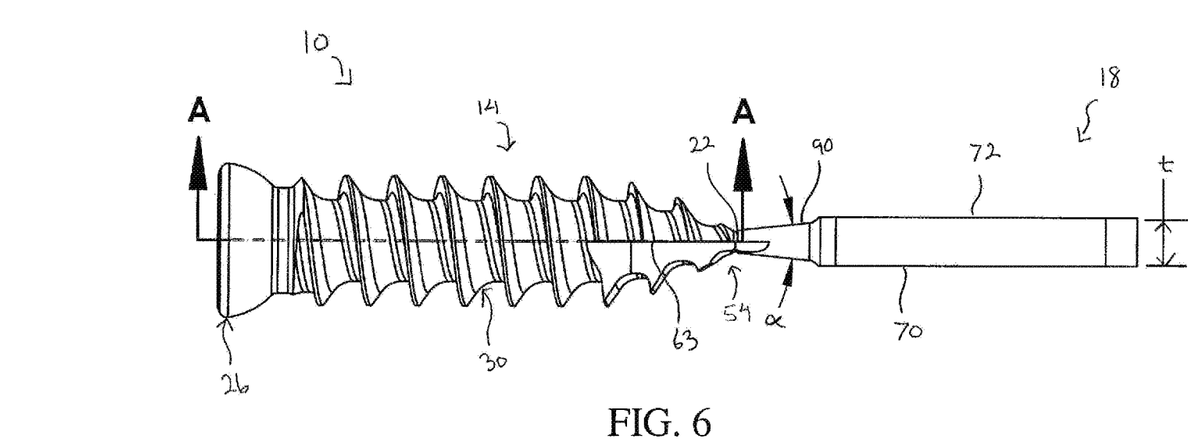
FIG. 6 is a top view of the bone screw depicted in FIG. 1 showing another view of the flute extending into the tip of the bone screw and into the frangible interface.

The tag body 18 in the form of the rectangular plate has a width (w) that extends parallel to the longitudinal axis 50 and a height (h) that extends perpendicular to the longitudinal axis 50, as shown in FIG. 1. The width of the tag body 18 is greater than the height such that the first surface 70 and the second surface 72 have a generally landscape orientation that is longer in a direction parallel to the longitudinal axis. A thickness (t) of the tag body 18 in a direction perpendicular to the first surface 70 and the second surface 72 is substantially less than the width and the height, as shown in FIGS. 3 and 6. In one specific embodiment of the generally rectangular tag body 18, the width is approximately 10 millimeters, the height is approximately 3.5 millimeters, and the thickness is approximately 1.5 millimeters. It will be appreciated that other shapes and dimension for the tag body 18 are contemplated.

The frangible interface 22 defines a region of reduced thickness 76 (FIG. 5) arranged between the tag body 18 and the screw tip 54 of the screw body 14. The frangible interface 22 is sufficiently rigid to maintain the connection of the tag body 18 to the screw body 14 during normal manipulation of the bone screw 10. However, the frangible interface 22 is also sufficiently thin to allow the frangible interface 22 to be fractured by application of a predefined mechanical force to the tag body 18. Once the frangible interface 22 is fractured, the tag body 18 can be removed from the screw body 14. The frangible interface 22 in one embodiment is configured to be fractured by twisting and/or bending the tag body 18. In this embodiment, the predefined mechanical force is generated by a person performing the twisting and/or bending of the tag body 18 with his or her hands. The predefined mechanical force can also be generated by use of a tool to perform the twisting and/or bending of the tag body 18. It will be appreciated that in some embodiments, the frangible interface 22 can also be severed directly, for example, by cutting the frangible interface 22 with a tool.

Figure 4:
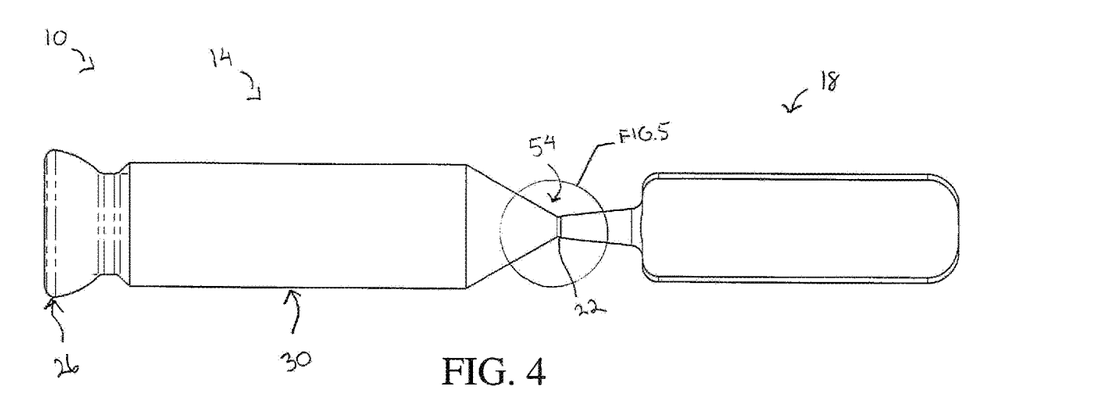
FIG. 4 is a side view of the bone screw of FIG. 1 shown in an intermediate stage of manufacture.
Figure 5:
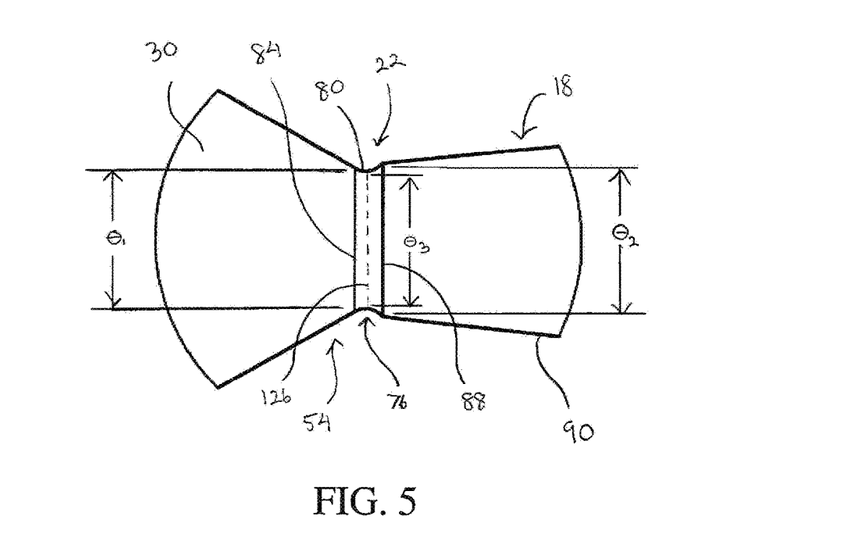
FIG. 5 is an enlarged view of a portion of FIG. 4 illustrating the frangible interface positioned between the tip of the bone screw and the frangible tag.

FIGS. 4 and 5 show the frangible interface 22 during an intermediate manufacturing step of the bone screw 10 when the external thread 58 has yet to be formed on the shaft portion 30. As illustrated, the frangible interface 22 is formed as a circumferential groove 80 that at least partially encircles the longitudinal axis 50 and defines the region of reduced thickness 76. The screw tip 54 defines a first circular edge 84 where the screw tip 54 abuts the frangible interface 22. The first circular edge has a first diameter $\theta_1$. The tag body 18 defines a second circular edge 88 where the tag body 18 abuts the frangible interface 22. The second circular edge has a second diameter $\theta_2$. The frangible interface 22 formed as the circumferential groove 80 has a circular cross section with a third diameter $\theta_3$. The third diameter $\theta_3$ is smaller than the first diameter $\theta_1$ and the second diameter $\theta_2$, and the first diameter $\theta_1$ is smaller than the second diameter $\theta_2$. In one specific embodiment, the second diameter $\theta_2$ is 0.70 millimeters and the third diameter $\theta_3$ is 0.63 millimeters. The first diameter $\theta_1$ in some embodiments, such as the bone screw depicted in FIGS. 9-11, can be equal to or greater than the second diameter $\theta_2$ while the third diameter $\theta_3$ remains smaller than the first diameter $\theta_1$ and the second diameter $\theta_2$.

The tag body 18 in one embodiment has a projection 90 that extends along the longitudinal axis 50 such that the frangible interface 22 is disposed between the screw tip 54 and the projection 90. The projection 90 in this embodiment has a conical shape and defines the second circular edge 88. The conical shape of the projection 90 has a draft angle α (FIG. 6), which in the embodiment shown is approximately 12° relative to the longitudinal axis 50. In other embodiments, the first edge 84, the second edge 88, and the region of reduced thickness 76 can have different geometries as long as the frangible interface 22 is configured to fracture between the screw body 14 and the tag body 18.

FIGS. 1-3, 6, and 7 show the bone screw 10 with the external thread 58, the first flute 63, and the second flute 65 formed on the shaft portion 30. The external thread 58 in a region proximate to the screw tip 54 has a thread profile with a thread portion that abuts the frangible interface 22. The thread profile in some embodiments varies circumferentially and longitudinally to provide the cutting edges 66 with different geometries so as to perform different functions. For example, as shown in FIG. 1, the first flute 63 exposes a first thread portion 96, a second thread portion 98, and a third thread portion 100 spaced from one another and arranged consecutively from the screw tip 54 towards the head portion 26 of the screw body 14. The first thread portion 96 abuts the frangible interface 22 and defines a first cutting edge 102. The second thread portion 98 and the third thread portion 100 define a second cutting edge 104 and a third cutting edge 106, respectively. As shown, the cutting edges 102, 104, 106 of each of the first thread portion 96, the second thread portion 98, and the third thread portion 100 are similarly configured as self-cutting threads.

As shown in FIG. 2, the second flute 65 exposes a fourth thread portion 110, a fifth thread portion 112, and a sixth thread portion 114 arranged consecutively from the screw tip 54 towards the head portion 26 of the screw body 14. The fourth thread portion 110 abuts the frangible interface 22 and defines a fourth cutting edge 116. The fifth thread portion 112 and the sixth thread portion 114 define a fifth cutting edge 118 and a sixth cutting edge 120, respectively. As shown, while the fifth cutting edge 118 and the sixth cutting edge 120 are similarly configured as self-cutting threads, the fourth cutting edge 116 is configured as a self-drilling thread with geometry similar to the tip of a center drill.

With continued reference to FIGS. 1-3, 6, and 7, the flute 63, 65 further extends into the frangible interface 22 such that a portion of the frangible interface 22 defines a further cutting edge 92. The further cutting edge 92 extends from the screw tip 54 past a fracture line 126 (FIGS. 4 and 7) defined by the frangible interface 22. The fracture line 126 represents a cross sectional area along which the frangible interface 22 is intended to fracture so that the tag body 18 is removable from the screw body 14. The fracture line 126 coincides with the region of reduced thickness 76. The fracture line 126 in the exemplary embodiment is positioned at a longitudinal midpoint between the screw tip 54 of the screw body 14 and the tag body 18. In other embodiments, the frangible interface 22 defines the fracture line 126 at any longitudinal position at or between the screw tip 54 and the tag body 18.

After the frangible interface 22 is fractured, a portion of the frangible interface 22 that remains between the screw tip 54 and the fracture line 126 forms frangible remains. The frangible remains define the further cutting edge 92, which is a sharp cutting edge disposed immediately adjacent the screw tip 54 of the screw body 14. The fracture line 126 in the exemplary embodiment is a straight line such that the frangible remains define a flat, planar surface at the screw tip 54 of the screw body 14 after the tag body 18 has been removed. In other embodiments, the fracture line 126 can have a curved shape such that the frangible remains define a curved surface, such as a hemispherical surface, at the screw tip 54 after the frangible interface 22 is fractured. It will be appreciated that the fracture line 126 can have different shapes such that the frangible remains define surfaces with different geometries than those described herein. The first embodiment of the bone screw 10 described with reference to FIGS. 1-8 is also referred to as a "sharp-tip" bone screw since the at least one of the cutting edges 116 at the screw tip 54 and the further cutting edge 92 at the frangible remains are sharp and facilitate a self-drilling action of the bone screw 10.

Figure 9:
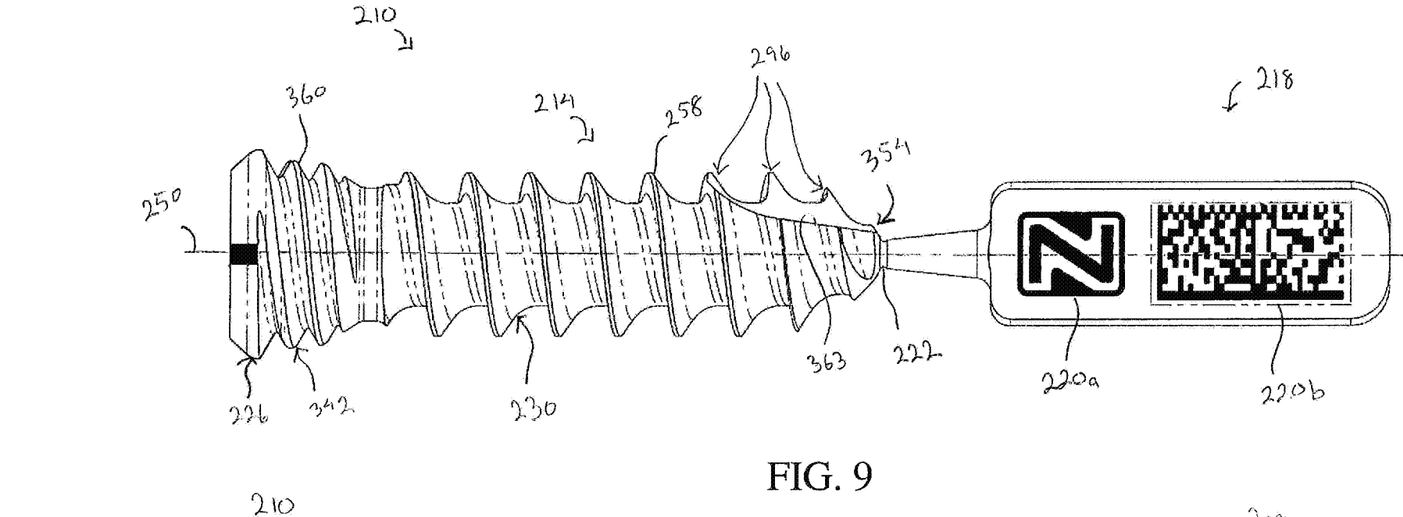
FIG. 9 is a side view of a blunt-tip bone screw incorporating the frangible tag of the present disclosure showing one side of the frangible tag.
Figure 10:
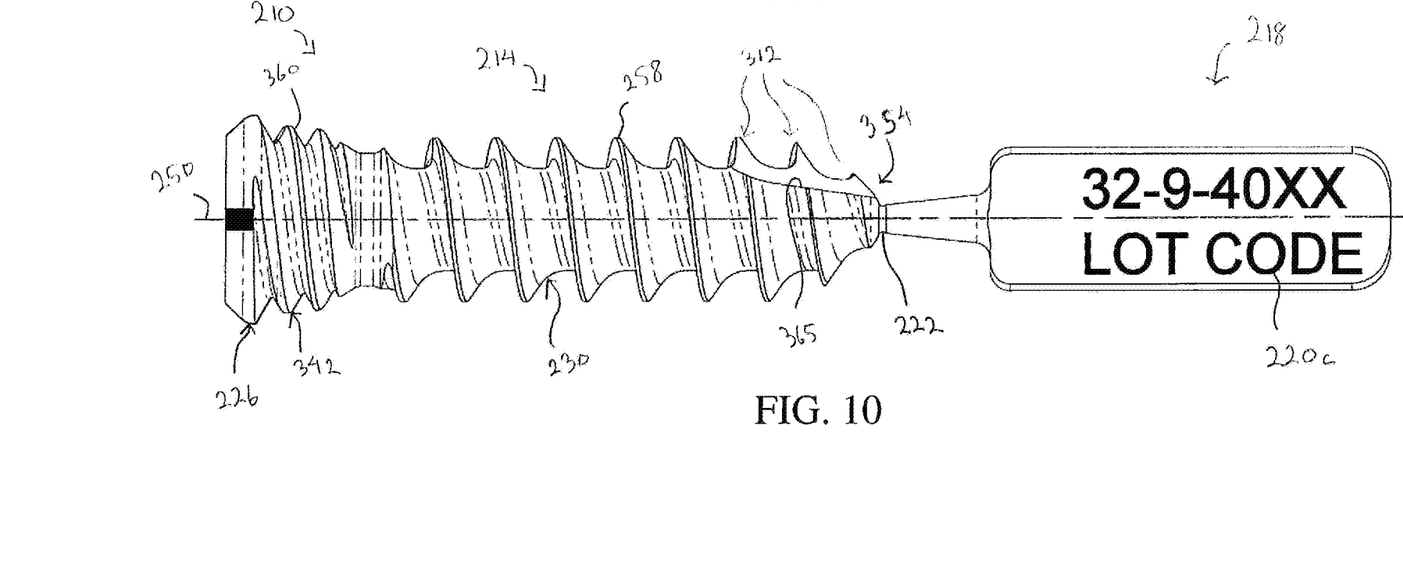
FIG. 10 is a side view of the bone screw depicted in FIG. 9 showing the opposite side of the frangible tag.
Figure 11:
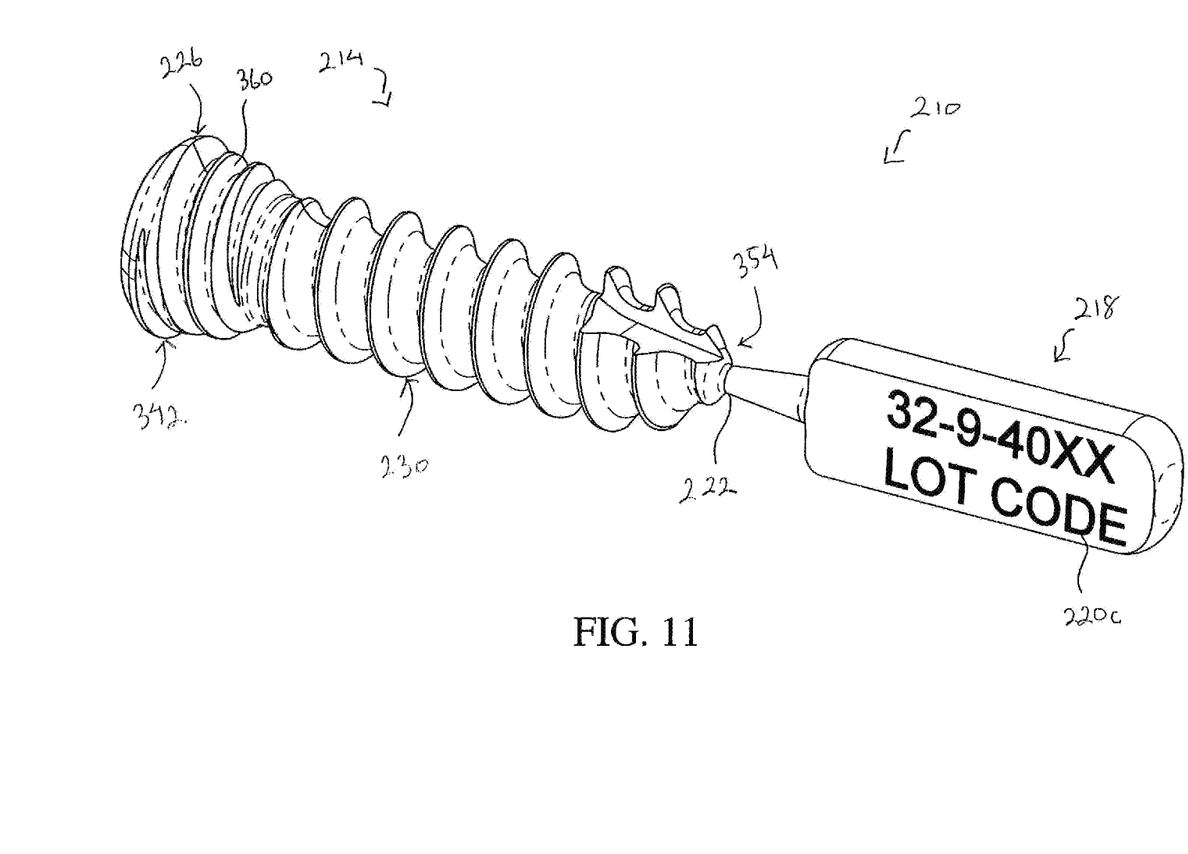
FIG. 11 is a perspective view of the bone screw depicted in FIG. 10 showing a flute extending into a tip of the bone screw.

FIGS. 9-11 depict a second embodiment of a bone screw 210 that meets the device tracking requirements set forth in the FDA regulations. In the figures, elements of the bone screw 210 that are similar to elements of the bone screw 10 of FIGS. 1-8 are designated by like reference numerals incremented by 200. For example, the screw body of the bone screw 10 is designated by reference numeral 14 while a similar screw body of the bone screw 210 is designated by reference numeral 214. New or modified elements of the bone screw 210 are designated by reference numerals incremented by 300.

The bone screw 210 shown in FIGS. 9-11 is similar to the bone screw 10 with a tag body 218 connected to the screw tip 354 of the screw body 214 at a frangible interface 222. The screw body 214 includes a head portion 226 and a threaded shaft portion 230 that extends from the head portion 226. The head portion 226 defines a driving feature in the form of a hexalobe interface similar to the hexalobe interface 36 of the bone screw 10. However, the outer surface 342 of the head portion 226 of the bone screw 210 defines a further external thread 360 that helically encircles the longitudinal axis 250. The further external thread 360 in the embodiment shown has a larger major diameter than the major diameter of the at least one external thread 258 on the threaded shaft portion 230.

Another difference between the bone screw 210 of FIGS. 9-11 and the bone screw 10 of FIGS. 1-8 is that the bone screw 210 does not have any cutting edges configured as a self-drilling thread at the screw tip 354. Instead, after the frangible interface 222 is fractured and the tag body 218 is removed from the screw body 214, the screw tip 354 has a flat surface that does not have any burrs or sharp edges that might otherwise compromise the screw tip 354 of the bone screw 210. This configuration at the screw tip 354 results in part because the first flute 363 (FIG. 9) and the second flute 365 (FIG. 10) do not extend into the frangible interface 222. The thread portions 296, 312 exposed by the first flute 363 and the second flute 365 are configured as self-cutting threads. The second embodiment of the bone screw 210 shown in FIGS. 9-11 is also referred to as a "blunt-tip" bone screw since the screw tip 354 has a flat surface after the tag body 218 is removed from the screw body 214. The tag body 218 of the bone screw 210 of FIGS. 9-11 is otherwise the same as the tag body 14 of the bone screw 10 of FIGS. 1-8.

The bone screws 10, 210 can be formed of materials conventional for use in implants, such as stainless steel or other durable surgical-grade materials, such as titanium and titanium-containing alloys. As shown in FIG. 4, the screw body 14, the tag body 18, and the frangible interface 22 are integrally formed in a conventional manufacturing process, after which the external thread 58 can be cut into the shaft portion 30 and the traceability information 20 added to the surfaces 70, 72 of the tag body 18. It can be appreciated that since the tag body 18 is not a structural or implanted component of the bone screw 10, the tag body 18 can be formed differently than the screw body 14, albeit as an integral extension of the screw body 14. Thus, the material of the tag body 18 can be less dense than the material of the screw body 14.

In one embodiment, the material of the screw body 14 has a first density that is greater than a second density of the same material of the tag body 18. This density variation can be accomplished in one embodiment by adding a filler to the material of the tag body 18, such as finely-dispersed gas or finely-dispersed solid particles. The tag body 18 can also be provided with perforations to reduce the material requirements for the bone screw 10. It is further contemplated that the tag body 14 can be incorporated into other small implants that lack adequate surface area to bear the UDI code and other information required by the FDA regulations.

Figure 12:
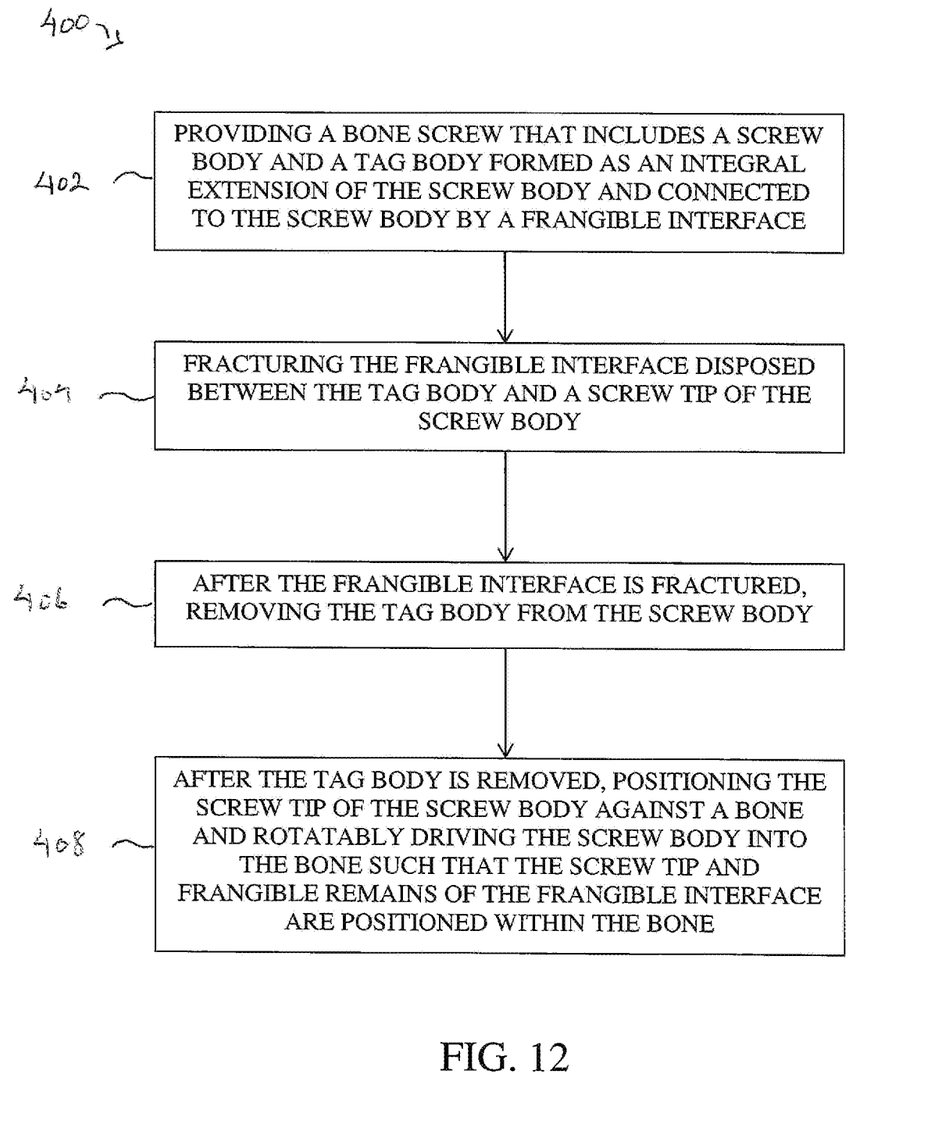
FIG. 12 depicts a method of implanting a bone screw that incorporates the frangible tag of the present disclosure.

FIG. 12 illustrates a method 400 of implanting a bone screw in a bone of a patient. The method includes providing a bone screw 10, 210 as illustrated in FIGS. 1-8 or FIGS. 9-11 (block 402). The method further includes fracturing a frangible interface of the bone screw that is disposed between the tag body and a screw tip of the screw body of the bone screw (block 404). The frangible interface is fractured by applying a predefined mechanical force to the tag body. After the frangible interface is fractured, the tag body is removed from the screw body (block 406). Once removed, the tag body with the UDI code and other traceability information can be stored with a file associated with the patient receiving the bone screw. After the tag body is removed from the screw body, the screw body is rotatably driven such that the screw tip and the frangible remains of the fractured frangible interface are positioned within the bone (block 408).

In one embodiment of the method, the step of fracturing the frangible interface includes forming a cutting edge with the frangible remains of the fractured frangible interface. After the frangible interface is fractured and the tag body is removed, the screw body is rotatably driven into the bone such that the cutting edge formed with the frangible remains removes bone material from the bone. In another embodiment of the method, the frangible interface is fractured such that a flat surface is formed at the screw tip after the tag portion is removed from the screw portion. In this embodiment, the method further includes forming a pilot hole in the bone prior to rotatably driving the screw portion into the bone.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A bone screw, comprising:
    a screw body having a head portion and a threaded shaft portion that extends along a longitudinal axis from the head portion to a screw tip of the screw body; and
    a tag body defining at least one surface configured to display traceability information for the bone screw, the tag body formed as an integral extension of the screw body and connected to the screw body via a frangible interface disposed between the tag body and the screw tip, the frangible interface configured to fracture upon application of a predefined mechanical force such that the tag body is removable from the bone screw,
    wherein a portion of at least one thread of the threaded shaft portion abuts the frangible interface at the screw tip,
    wherein at least one flute extends through a portion of the shaft portion and forms a cutting edge on the at least one thread, the cutting edge configured to remove bone material when the screw body is threaded into a bone, and
    wherein the at least one flute extends over the frangible interface such that a portion of the frangible interface defines a further cutting edge extending from the screw tip after the frangible interface is fractured and the tag body is removed from the bone screw.

2. The bone screw of claim 1, wherein the frangible interface defines a region of reduced thickness between the screw tip and the tag body.

3. The bone screw of claim 2, wherein a circumferential groove that at least partially encircles the longitudinal axis at the frangible interface defines the region of reduced thickness.

4. The bone screw of claim 1, wherein the screw tip is configured to have a flat surface after the frangible interface is fractured and the tag body is removed from the bone screw.

5. The bone screw of claim 1, wherein the tag body has a projection that extends along the longitudinal axis, the frangible interface disposed between the projection and the screw tip.

6. The bone screw of claim 1, wherein the tag body defines opposed surfaces configured to display the traceability information for the bone screw.

7. A bone screw, comprising:
    a screw body having a head portion and a threaded shaft portion that extends along a longitudinal axis from the head portion to a screw tip of the screw body; and
    a tag body defining at least one surface configured to display traceability information for the bone screw, the tag body formed as an integral extension of the screw body and connected to the screw body via a frangible interface disposed between the tag body and the screw tip, the frangible interface configured to fracture upon application of a predefined mechanical force such that the tag body is removable from the bone screw,
    wherein the screw body, the tag body, and the frangible interface are formed from the same material, the material having a variable density such that the material of the screw body has a first density that is greater than a second density of the material of the tag body and the frangible interface.

8. The bone screw of claim 1, wherein tag body includes a plurality of perforations.

9. The bone screw of claim 1, wherein the tag body has a rectangular shape with a width extending parallel to the longitudinal axis and a height extending perpendicular to the longitudinal axis, the width being greater than the height.

10. The bone screw of claim 1, wherein:
    the screw tip defines a first circular edge where the screw tip abuts the frangible interface, the first circular edge having a first diameter,
    the tag body defines a second circular edge where the tag body abuts the frangible interface, the second circular edge having a second diameter, and
    the frangible interface has a circular cross section with a third diameter that is smaller than the first and second diameters.

11. The bone screw of claim 7, wherein the frangible interface defines a region of reduced thickness between the screw tip and the tag body.

12. The bone screw of claim 11, wherein a circumferential groove that at least partially encircles the longitudinal axis at the frangible interface defines the region of reduced thickness.

13. The bone screw of claim 7, wherein the screw tip is configured to have a flat surface after the frangible interface is fractured and the tag body is removed from the bone screw.

14. The bone screw of claim 7, wherein the screw tip is configured to have at least one cutting edge after the frangible interface is fractured and the tag body is removed from the bone screw.

15. The bone screw of claim 7, wherein the tag body defines opposed surfaces configured to display the traceability information for the bone screw.

* * * * *